United States Patent [19]
Tsubota et al.

[11] Patent Number: 5,834,227
[45] Date of Patent: Nov. 10, 1998

[54] KIT FOR ASSAYING CREATINE KINASE

[75] Inventors: Hiroyuki Tsubota; Reiko Shimada, both of Tokyo, Japan

[73] Assignee: Iatron Laboratories, Inc., Tokyo, Japan

[21] Appl. No.: 507,229

[22] PCT Filed: Dec. 19, 1994

[86] PCT No.: PCT/JP94/02136

§ 371 Date: Aug. 18, 1995

§ 102(e) Date: Aug. 18, 1995

[87] PCT Pub. No.: WO95/17520

PCT Pub. Date: Jun. 29, 1995

[30] Foreign Application Priority Data

Dec. 20, 1993 [JP] Japan .................................. 5-344824

[51] Int. Cl.$^6$ .............................. C12Q 1/50; C12Q 1/32; C12N 9/04; C12N 9/12
[52] U.S. Cl. .............................. 435/17; 435/26; 435/189; 435/194; 536/26.22; 536/26.24; 562/553
[58] Field of Search ................................ 435/17, 26, 189, 435/194; 536/26.22, 26.24; 562/553

[56] References Cited

U.S. PATENT DOCUMENTS 5,587,296  12/1996  Tsubota ...................................... 435/14

OTHER PUBLICATIONS

Chemical Abstract 108: 71027, Kondo et al., J. Clin. Biochem. Nutr. 3(1):17–25, 1987.

*Primary Examiner*—Gary L. Kunz
*Attorney, Agent, or Firm*—Sughrue, Mion, Zinn, Macpeak & Seas, PLLC

[57] ABSTRACT

A reagent for assaying creatine kinase, which contains glucokinase or hexokinase, glucose-6-phosphate dehydrogenase, adenosine 5'-diphosphate, creatine phosphate, oxidized nicotinamide adenine dinucleotide phosphate, magnesium salt, and glucose; and which comprises a first liquid reagent having a pH value of 7.5 to 10 and containing at least glucokinase and/or hexokinase, glucose-6-phosphate dehydrogenase, adenosine 5'-diphosphate and creatine phosphate, and a second liquid reagent having a pH value of 2 to 5 and containing at least oxidized nicotinamide adenine dinucleotide phosphate. The present reagent can be stably stored in the form of liquid for a long period of time at normal or low temperature in dark or light place. Therefore, it can be used without dissolution procedure after being preserved for a long term at the site of clinical examination and is also applicable to automatic analyzers.

10 Claims, 3 Drawing Sheets

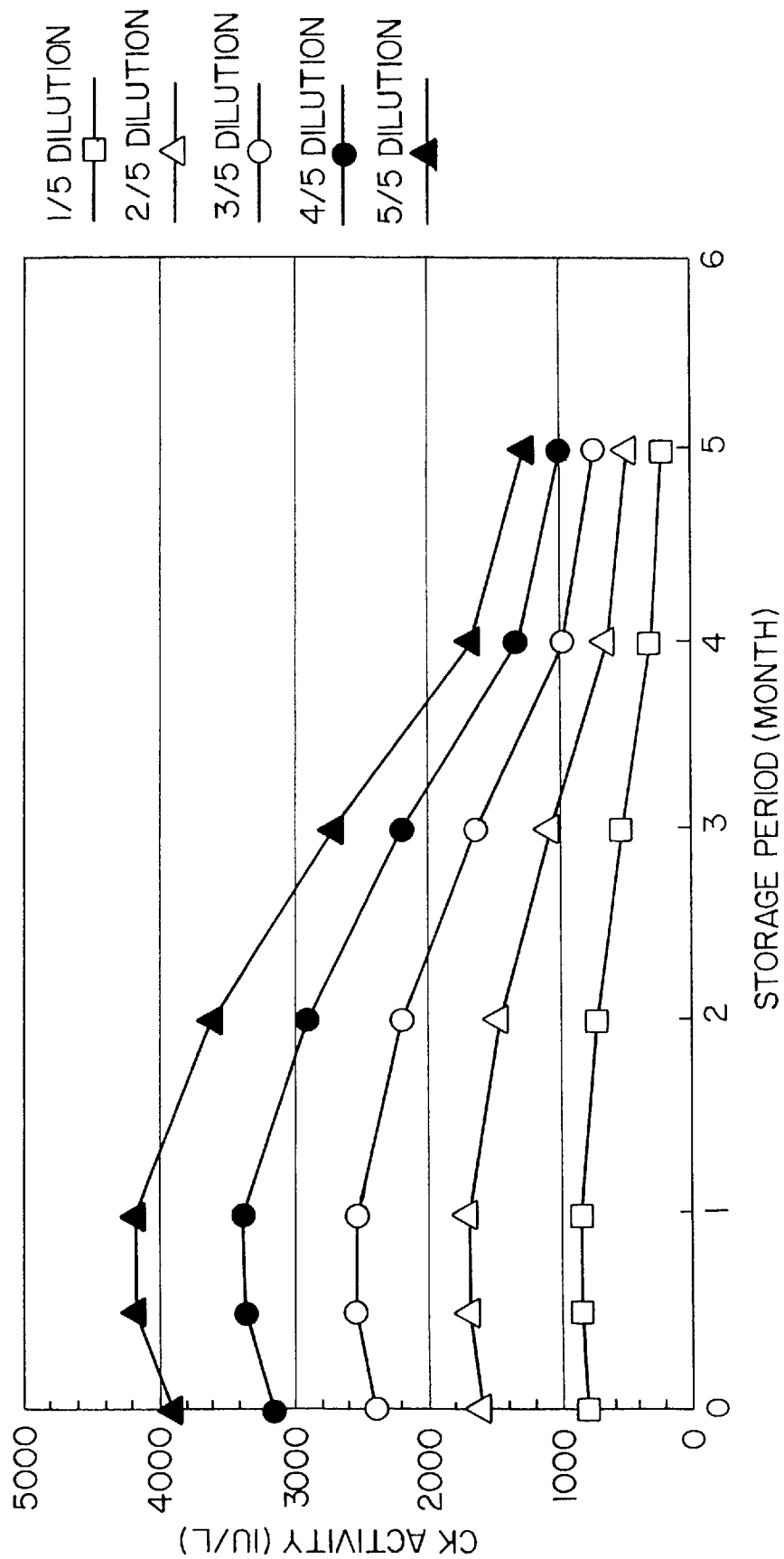

KIT FOR ASSAYING CREATINE KINASE

This case is a 371 of PCT/JP94/02136 filed Dec. 19, 1994.

TECHNICAL FIELD

The present invention relates to a reagent for assaying creatine kinase (hereinafter referred to as CK) in a sample, more particularly, an improved liquid reagent for assaying CK, which is stable over a long period.

BACKGROUND ART

CK is distributed in skeletal, cardiac and smooth muscles and a brain. CK is an important enzyme taking part in energy metabolism, and is released into blood from tissues when a muscle or heart is suffered from disease. It is important to assay CK activity as indices for various diseases.

CK catalyzes following reaction:

ATP+creatine→ADP+creatine phosphate (forward reaction) ADP+creatine phosphate→ATP+creatine (reverse reaction) wherein ATP is adenosine 5'-triphosphate, and ADP is adenosine 5'-diphosphate.

In the assay of CK, the products of the forward and reverse reactions are used. According to the reaction product to be determined, the assay is broadly classified into the following four methods:

(1) As a method for determining ADP, for example, the decrease of the reduced nicotinamide adenine dinucleotide (NADH) is measured, using pyruvate kinase and lactate dehydrogenase as conjugated enzymes.

(2) As a method for determining creatine phosphate, for example, inorganic phosphorus produced by hydrolyzing creatine phosphate is measured.

(3) As a method for determining ATP, for example, the increase of the reduced nicotinamide adenine dinucleotide phosphate (hereinafter referred to as NADPH) is measured, using mainly hexokinase (hereinafter referred to as HK) or glucokinase (hereinafter referred to as GlcK) and glucose-6-phosphate dehydrogenase (hereinafter referred to as G6PDH) as conjugated enzymes.

(4) As a method for determining creatine, for example, creatinine converted from creatine produced from the CK enzyme reaction is measured by means of Jaffe's method or the like.

Of the above methods (1) to (4), the method (3) for determining ATP has been widely used, and recommended as a standard method for determining CK activity by Japanese Society of Clinical Chemistry (JSCC).

The reactions for determining CK activity in HK-G6PDH method which is a typical example of the method (3) for determining ATP are as follows:

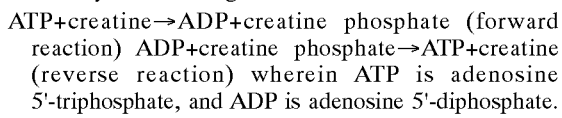

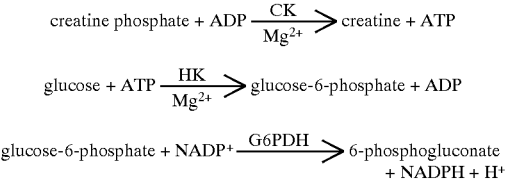

wherein NADP$^+$ is oxidized nicotinamide adenine dinucleotide phosphate.

The HK-G6PDH method is very excellent for determining CK activity. However, very unstable enzymes and substrates were used, and thus, a long term storage was difficult. Therefore, the enzymes, substrates and the like are supplied in the form of lyophilized products. Further, stabilizing conditions for the reagents widely vary with their combinations. Therefore, it was difficult to maintain stability of liquid reagent for a long period of time by conventional combinations.

With the spread of an automatic analyzer, the reagent composition used in the method for determining CK activity has been converted from a one-component form to a two-component form. According to the conventional combination of the two-component form, a reagent for initiating the reaction (second reagent) which is a substrate for determining CK generally contains creatine phosphate, and a first reagent contains all the remaining components. However, the storage stability as a liquid reagent was very poor. Further, some second reagents contained HK and/or G6PDH, there was a problem in the stabilities of the enzymes. Furthermore, it was not possible to obtain sufficient stability by other combinations.

Recently, it is desired to improve the workability for users, by providing the reagents in a liquid form from a supplier, instead of preparing the liquid reagent when used.

The stability of the enzymes per se has been improved by removing the interfering contaminant enzymes by sophisticated purification of the enzymes or by using heat resistant enzymes, for example, glucokinase (hereinafter referred to as GlcK) derived from Bacillus stearothermophilus, HK obtained from recombinant yeast or chemically modified enzymes thereof. However, it was difficult to obtain a sufficient storage stability for liquid reagents by such enzymes. Particularly, the inventors of the present invention found that, in the reagent used in HK-G6PDH method, the enzymes and substrates which are stable alone respectively, become unstable when contained with each other in a same liquid. Namely, the inventors found that the components other than the enzymes, i.e., the substrates such as NADP$^+$ and creatine phosphate are one of the greatest destabilizing factors. Therefore, it is necessary to arrange the preferred combinations and atmosphere (concentration or pH) for each substrate, and the arrangement is very important for liquefying the reagent.

DISCLOSURE OF INVENTION

The inventors of the present invention engaged in various in-depth studies to solve the above problems in the prior art and as a result discovered a reagent composition having sufficient storage stability for a long period of time when supplied in the form of a liquid reagent. The present invention is based on this discovery.

Accordingly, the present invention relates to a reagent for assaying creatine kinase, which contains glucokinase or hexokinase, glucose-6-phosphate dehydrogenase, adenosine 5'-diphosphate, creatine phosphate, oxidized nicotinamide adenine dinucleotide phosphate, magnesium salt, and glucose; and which comprises a first liquid reagent having a pH value of 7.5 to 10 and containing at least glucokinase and/or hexokinase, glucose-6-phosphate dehydrogenase, adenosine 5'-diphosphate and creatine phosphate, and a second liquid reagent having a pH value of 2 to 5 and containing at least oxidized nicotinamide adenine dinucleotide phosphate.

BRIEF DESCRIPTION OF DRAWINGS

FIG. 3 is a graph illustration stability when a comparative reagent was stored at 10° C.

BEST MODE FOR CARRYING OUT THE INVENTION

Figure 1:
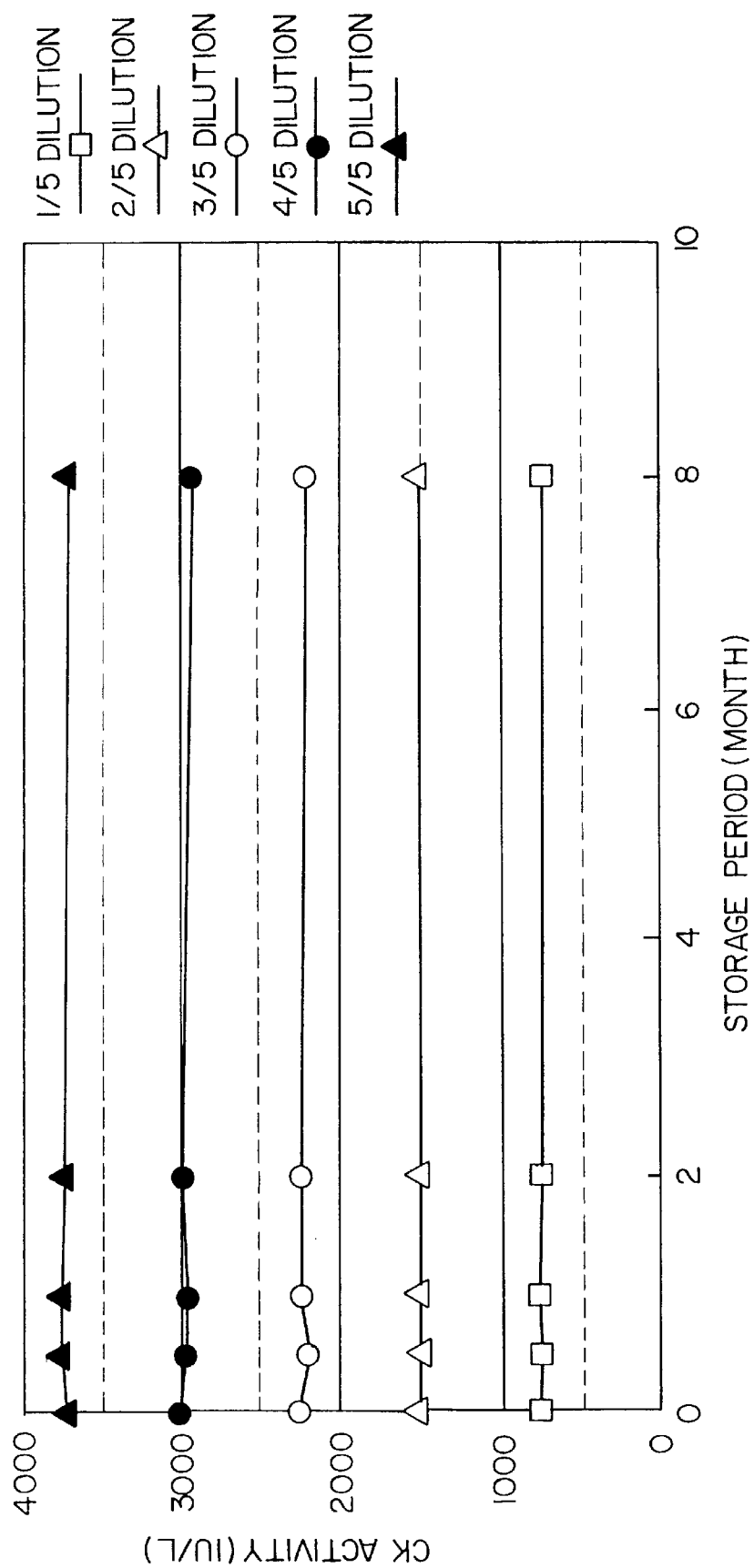
FIG. 1 is a graph illustrating stability when the reagent of the present invention was stored at 4° C.

The present invention will be explained in detail hereinafter.

The reagent of the present invention comprises (1) a first liquid reagent containing at least GlcK or HK, and G6PDH, ADP and creatine phosphate, and having a pH value of 7.5 to 10, and (2) a second liquid reagent containing at least NADP, and having a pH value of 2 to 5.

The substrate, glucose, may be contained in the first reagent and/or the second reagent. It is preferable to contain glucose only in the first reagent together with Glck or HK, because of the stability of the enzymes. The magnesium salt may be contained in the first reagent and/or the second reagent. However, the tendency of slight deterioration of creatine phosphate by the action of the magnesium salt is observed. Therefore, it is preferable to contain the magnesium salt principally in the second reagent for maintaining the stability in liquid for a long period of time (for example, for 6 months or more).

Because creatine phosphate is stable in an alkaline buffer (pH about 7.5 to 10), the first reagent containing at least GlcK or HK, G6PDH, and ADP may be dissolved in a buffer having pH 7.5 to 10. If the pH of the buffer is more than 10, the stability of the enzymes becomes worse. If the pH of the buffer is less than 7.5, the stability of, in particular, creatine kinase becomes insufficient. It is possible to use any buffer having said pH range, but preferably Good's buffer, more particularly HEPES buffer (pH 8.5) (hereinafter referred to as HEPES).

As the HK and the GlcK, it is possible to use enzymes having a pH stability in a weak alkaline range (pH 7 to 9.5), for example, HK derived from yeast or GlcK derived from Bacillus stearothermophilus. The HK and/or the GlcK may be added in an amount of about 0.1 U/ml or more, preferably about 0.1 to 40 U/ml, most preferably about 0.2 to 10 U/ml. If the amount of the HK and/or the GlcK is less than 0.1 U/ml, sufficient activities for determining CK cannot be obtained. If the amount is more than 40 U/ml, there is no problem in the measuring process. However, it is not necessary to add an excess amount, in view of contamination of impurities and the cost of the enzymes used. As the G6PDH, an enzyme which has a pH stability in the above weak alkaline range, for example, an enzyme derived from Leuconostoc mesenteroides is suitable. The enzyme may be added in an amount of about 0.1 U/ml or more, preferably about 0.1 to 40 U/ml, more preferably about 0.2 to 10 U/ml. If the amount of the G6PDH is less than 0.1 U/ml, sufficient activities for determining CK cannot be obtained. If the amount is more than 40 U/ml, there is no problem in the measuring process. However, it is not necessary to add an excess amount, in view of contamination of impurities and the cost of the enzymes used.

It is possible to add creatine phosphate to the first reagent in an amount of about 2 to 200 mM, preferably about 10 to 100 mM. If the amount of creatine phosphate is less than 2 mM, sufficient enzymatic reactions for determining CK are not performed. If the amount is more than 200 mM, substrate inhibition occurs in addition to contamination of impurities and the cost. It is possible to add ADP to the first reagent in an amount of about 0.1 mM or more, preferably about 0.1 to 20 mM, more preferably about 0.2 to 10 mM. If the amount of ADP is less than 0.1 mM, sufficient enzymatic reactions for determining CK are not performed. If the amount is more than 20 mM, there is no problem in the measuring process. However, it is not necessary to add an excess amount, in view of contamination of impurities and the cost. It is possible to add glucose to the first reagent in an amount of about 1 mM or more, preferably about 1 to 1000 mM, more preferably 2.5 to 250 mM. If the amount of glucose is less than 1 mM, sufficient enzymatic reactions for determining CK are not performed. If the amount is more than 1000 mM, there is no problem in the measuring process. However, it is not preferable in view of contamination of impurities and the cost. When the magnesium salt is contained in the first reagent, any inorganic or organic water-soluble magnesium salt, such as magnesium chloride, acetate or sulfate, may be used. The concentration of the magnesium salt is preferably about 0.5 mM or more, more preferably about 1 to 100 mM, most preferably 5 to 60 mM. If the amount of the magnesium salt is less than 0.5 mM, sufficient enzymatic reactions by CK and HK or Glck are not performed. If the amount is more than 100 mM, there is no problem in the measuring process. However, it is not preferable in view of contamination of impurities and the cost, and particularly, the tendency of deterioration of creatine phosphate during a storage in a liquid form for a long period of time, for example, for 6 months or more. If necessary, the first reagent may contain a chelating agent, such as etylenediaminetetraacetic acid (hereinafter referred to as EDTA), a preservative, such as 6-phosphogluconolactonase, so as to improve measuring accuracy as in Japanese Unexamined Patent Publication (Kokai) No. 4-287698.

$NADP^+$ contained in the second reagent is stable in an acidic buffer, and thus, $NADP^+$ is dissolved in a buffer of pH 2 to 5. $NADP^+$ becomes unstable outside the pH range. As the buffer, any buffer usually used in the above pH range may be used. It is preferable to use, for example, an acetate buffer (pH 3). The buffer concentration of the second reagent should be adjusted so that the pH of the mixture together with the first reagent becomes 6 to 7. NADP may be used in an amount of about 0.1 mM or more, preferably about 0.1 to 20 mM, more preferably about 0.5 to 15 mM. If the amount of NADP is less than 0.1 mM, sufficient enzymatic reactions by G6PDH are not sufficiently performed. If the amount is more than 20 mM, there is no problem in the measuring process. However, it is not preferable in view of contamination of impurities and the cost. When the magnesium salt is contained in the second reagent, any inorganic or organic water-soluble magnesium salt, such as magnesium chloride, acetate or sulfate, may be used. The concentration of the magnesium salt is preferably about 0.5 mM or more, more preferably about 1 to 100 mM, most preferably 5 to 60 mM. If the amount of the magnesium salt is less than 0.5 mM, sufficient enzymatic reactions by CK and HK or Glck are not performed. If the amount is more than 100 mM, there is no problem in the measuring process. However, it is not preferable in view of contamination of impurities and the cost. When glucose is contained in the second reagent, the amount used may be about 1 mM or more, preferably about 1 to 1000 mM, more preferably 2.5 to 250 mM. If the amount of glucose is less than 1 mM, sufficient enzymatic reactions for measuring CK are not performed. If the amount is more than 1000 mM, there is no problem in the measuring process. However, it is not preferable in view of contamination of impurities and the cost. If necessary, the second reagent may contain an SH compound, such as N-acetylcysteine, which is an agent for activating CK, EDTA, a preservative, or the like. When glucose is contained in the first and second reagents, the amount in total may be about 1 mM or more, preferably about 1 to 1000 mM, more preferably 2.5 to 250 mM. If the total amount of glucose is less than 1 mM, sufficient enzymatic reactions for measuring CK are not performed. If the total amount is more than 1000 mM, there is no problem in the measuring process. However, it is not preferable in view of contamination of impurities and the cost. When the magnesium salt is contained in the first and second reagents, any inorganic or organic water-soluble magnesium salt, such as magnesium chloride, acetate or sulfate, may be used. The total concentration of the magnesium salt is preferably about 0.5 mM or more, more preferably about 1 to 100 mM, most preferably 5 to 60 mM. If the total amount of the magnesium salt is less than 0.5 mM, sufficient enzymatic reactions by CK and HK or Glck are not performed. If the total amount is more than 100 mM, there is no problem in the measuring process. However, it is not preferable in view of contamination of impurities and the cost, and particularly, an adverse effect on creatine phosphate during storage for a long period of time, for example, for 6 months or more, by the large amount of the magnesium salt added in the first reagent, as explained above. When the magnesium salt is contained in both of the first and second reagents, it is preferable in view of stability that the amount contained in the second reagent is larger that that contained in the first reagent.

The liquid reagent comprising the above components according to the present invention is extremely improved in the storage stability for a long time in comparison with the conventional reagents. It is a novel and unique idea that NADP is a coenzyme of the conjugated enzyme, G6PDH, is used as an initiating reagent, i.e., the second reagent.

EXAMPLE

The present invention now will be further illustrated by, but is by no means limited to, the following examples.

Example 1

Preparation of reagents

The first and second reagents having following compositions were prepared.

First agent
  50 mM HEPES buffer (pH 8.5)
  30 mM creatine phosphate
  25 mM glucose
  2 mM EDTA
  2 mM ADP
  6 mM AMP (adenosine 5'-monophosphate)
  12.5 μM diadenosine 5'-pentaphosphate
  4 U/ml GlcK
  1 U/ml G6PDH
Second reagent
  103 mM acetate buffer (pH 3.0)
  2 mM EDTA
  10 mM NADP
  100 mM N-acetylcysteine
  50 mM magnesium chloride
(2) Stability The first and second reagents prepared in the above were stored separately at 4° C. or 10° C. After the predetermined periods (2 weeks, 1, 2 or 8 months), ere taken and CK activities were measured under the conditions, using, as a specimen, 5-stepwise series of human sera containing high units (3800 IU/L) with physiological saline.

The measuring procedure comprised adding 320 μl of the first reagent to 8 μl of the specimen, incubating the whole at 37° C. for 5 minutes, adding 80 μl of the second reagent, incubating the whole at 37° C. for 5 minutes, and measuring the absorbance at 340 nm.

Figure 2:
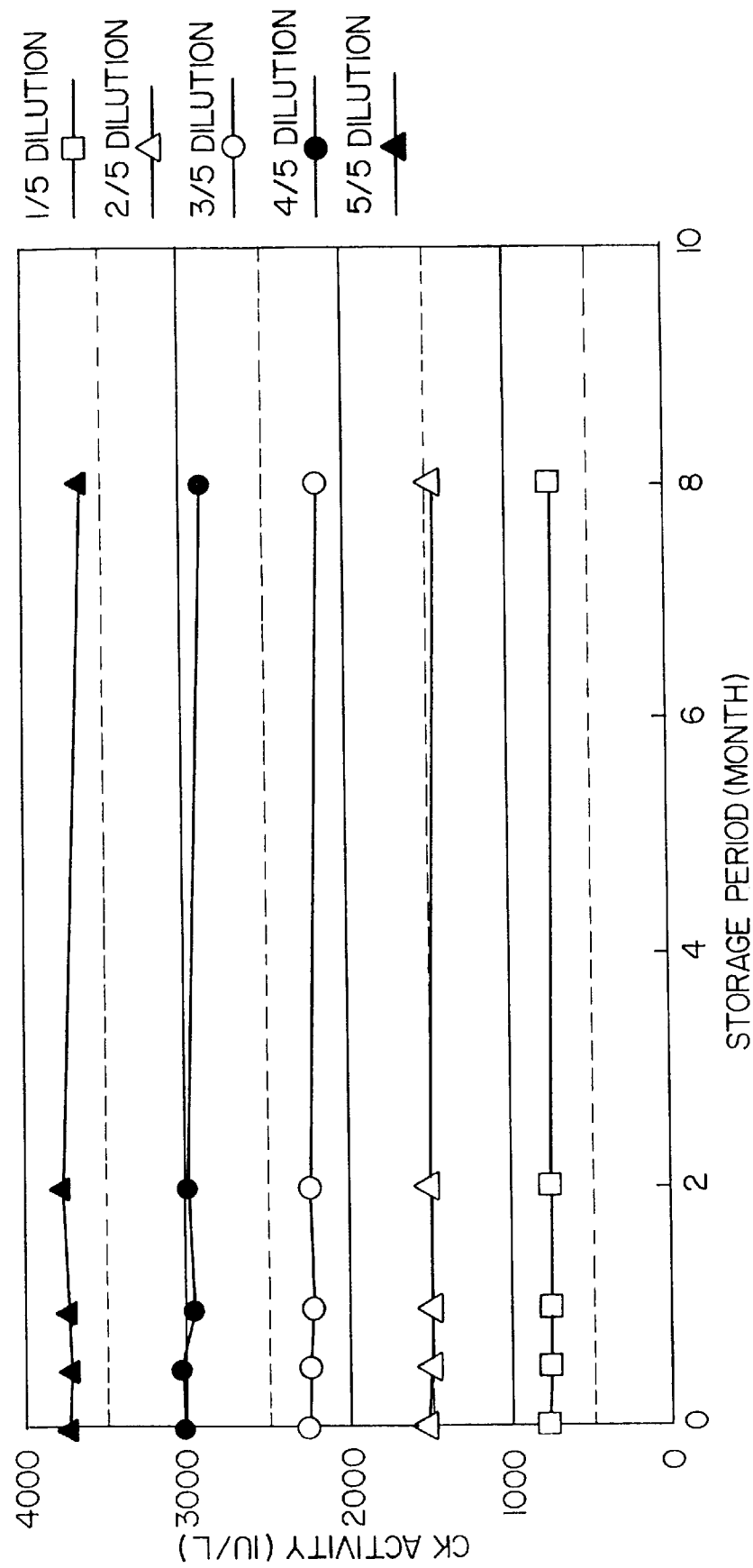
FIG. 2 is a graph illustrating stability when the reagent of the present invention was stored at 10° C.

The results of the assays are shown in FIG. 1 (reagents stored at 4° C.) and FIG. 2 (reagents stored at 10° C.), respectively.

Comparative Example

The first and second reagents having following compositions were prepared for comparison.

First reagent
  75 mM imidazole buffer (pH 6.7)
  25 mM glucose
  2 mM EDTA
  2 mM ADP
  6 mM AMP
  12.5 μM diadenosine 5'-pentaphosphate
  2.5 mM NADP
  25 mM N-acetylcysteine
  4 U/ml ClcK
  1 U/ml G6PDH
Second reagent
  25 mM tris buffer (pH 7.5)
  130 mM creatine phosphate
  50 mM magnesium acetate The first and second reagents were stored separately at 10° C. After the elapse of predetermined periods (2 weeks, 1, 2, 3, 4 or 5 months), samples were taken and CK activities were measured as in Example 1 to evaluate the stabilities of the reagents. The results are shown in FIG. 3.

INDUSTRIAL APPLICABILITY

The reagent for assaying CK according to the present invention can be stably stored in the form of liquid for a long period of time (at least for about one year) at normal or low temperature in either of dark or light place. Therefore, the reagent can be used without dissolution step after being preserved in the form of liquid for a long period of time where clinical examination is carried out, and the reagent is also applicable to automatic analyzers.

As above, the present invention is explained with reference to particular embodiments, but modifications and improvements obvious to those skilled in the art are included in the scope of the present invention.

We claim:

1. A kit for assaying creatine kinase, comprising the following first and second reagent solutions: the first reagent solution having a pH value of 7.5 to 10 and containing at least glucose, glucokinase and/or hexokinase, glucose-6-phosphate dehydrogenase, adenosine 5'-diphosphate and creatine phosphate, and the second reagent solution having a pH value of 2 to 5 and containing at least oxidized nicotinamide adenine dinucleotide phosphate and an SH compound for activating creatine kinase, wherein one or both of the first and second reagent solutions further contains magnesium salt.

2. The kit according to claim 1, wherein the first reagent solution contains glucokinase or hexokinase in an amount of about 0.1 U/ml or more.

3. The kit according to claim 1, wherein the first reagent solution contains glucose-6-phosphate dehydrogenase in an amount of about 0.1 U/ml or more.

4. The kit according to claim 1, wherein the first reagent solution contains adenosine 5'-diphosphate in an amount of about 0.1 mM or more.

5. The kit according to claim 1, wherein the first reagent solution contains creatine phosphate in an amount of 2 mM or more.

6. The kit according to claim 1, wherein the second reagent solution contains oxidized nicotinamide adenine dinucleotide phosphate in an amount of about 0.1 mM or more.

7. The kit according to claim 1, wherein only the second reagent solution contains magnesium salt.

8. The kit according to claim 1, wherein only the second reagent solution contains magnesium chloride and said magnesium chloride is present in an amount of about 0.5 mM or more.

9. The kit according to claim 1, wherein concentrations of the first and second reagent solutions are adjusted so that the pH of a mixture of the first and second reagent solutions is 6 to 7.

10. The kit according to claim 1, wherein the SH compound for activating creatine kinase is N-acetylcysteine.

* * * * *